United States Patent [19]

Yukinaga et al.

[11] 4,293,328
[45] Oct. 6, 1981

[54] N-(5-T-BUTYL-3-ISOXAZOLYL)ALKONAMIDE DERIVATIVES AND HERBICIDAL COMPOSITIONS CONTAINING THEM

[75] Inventors: Hisajiro Yukinaga, Kusatsu; Shinzaburo Sumimoto; Ichiro Ishizuka, both of Osaka; Jitsuo Sugita, Ikeda, all of Japan

[73] Assignee: Shionogi & Co., Ltd., Osaka, Japan

[21] Appl. No.: 914,749

[22] Filed: Jun. 7, 1978

Related U.S. Application Data

[60] Continuation-in-part of Ser. No. 836,238, Sep. 23, 1977, Pat. No. 4,111,680, which is a division of Ser. No. 667,033, Mar. 15, 1976, Pat. No. 4,062,861, which is a continuation of Ser. No. 491,491, Jul. 23, 1974, abandoned.

[30] Foreign Application Priority Data

Jul. 27, 1973 [JP] Japan .................................. 48-85339

[51] Int. Cl.³ .................... A01N 43/80; C07D 261/14
[52] U.S. Cl. ........................................ 71/88; 548/246
[58] Field of Search ...................... 260/307 H; 71/88; 548/246

[56] References Cited

U.S. PATENT DOCUMENTS

| | | | |
|---|---|---|---|
| 3,544,584 | 12/1970 | Iwai et al. | 260/307 H |
| 4,028,376 | 6/1977 | Yukinaga et al. | 71/88 |
| 4,062,861 | 12/1977 | Yukinaga et al. | 548/246 |
| 4,116,671 | 9/1978 | Yukinaga et al. | 548/246 |

FOREIGN PATENT DOCUMENTS

| | | | |
|---|---|---|---|
| 18-14218 | 6/1943 | Japan | 260/307 H |
| 40-8540 | 5/1965 | Japan | 548/246 |
| 50-133256 | 11/1975 | Japan | 260/307 H |
| 51-63170 | 1/1976 | Japan | 548/246 |

*Primary Examiner*—Donald G. Daus
*Assistant Examiner*—D. B. Springer
*Attorney, Agent, or Firm*—Wenderoth, Lind & Ponack

[57] ABSTRACT

Herbicidal compounds represented by the formula:

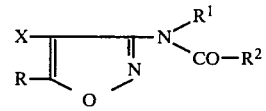

wherein R is t-butyl; $R^1$ is hydrogen or methyl; $R^2$ is alkyl ($C_2$ to $C_6$), alkenyl ($C_3$ to $C_4$) or cyclopropyl; and X is hydrogen or halogen; and herbicidal compositions containing them.

11 Claims, No Drawings

N-(5-T-BUTYL-3-ISOXAZOLYL)ALKANAMIDE DERIVATIVES AND HERBICIDAL COMPOSITIONS CONTAINING THEM

This application is a continuation-in-part of Ser. No. 836,238, filed Sept. 23, 1977, now U.S. Pat. No. 4,111,680, which is a division of Ser. No. 667,033, filed Mar. 15, 1976, now U.S. Pat. No. 4,062,861, which is a continuation of Ser. No. 491,491, filed July 23, 1974, now abandoned.

The present invention relates to N-(5-t-butyl-3-isoxazolyl)alkanamide derivatives and herbicidal compositions containing them.

According to the present invention there is provided a compound represented by the formula:

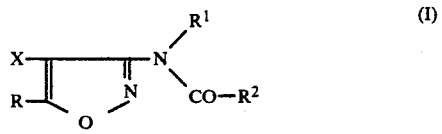

wherein R is t-butyl; $R^1$ is hydrogen or methyl; $R^2$ is alkyl ($C_2$ to $C_6$), alkenyl ($C_3$ to $C_4$) or cyclopropyl; and X is hydrogen or halogen.

In the above definition, each range of the number of carbon atoms given in parenthesis refers to the preferred range for the respective groups.

Among suitable alkyls are ethyl, propyl, i-propyl, butyl, i-butyl, t-butyl, pentyl and hexyl. Alkenyl includes allyl, isopropenyl, butenyl and butadienyl. Halogen may, for example, be chlorine or bromine.

The isoxazole derivatives (I) of the present invention show excellent herbicidal activity and have very low toxicity towards humans, animals and fishes. It has also been discovered that the isoxazole derivatives (I) are smoothly decomposed or degraded in soil after application as herbicides.

The isoxazole derivatives (I) can be prepared according to the following synthetic routes:

First route

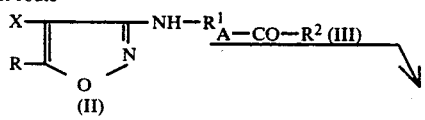

Second route

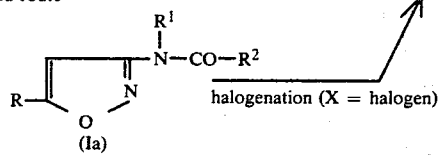

wherein A is a residue of reactive group such as halogen (e.g. chlorine, bromine) or ester (e.g. tosyloxy, mesyloxy, —O—CO—$R^2$), R, $R^1$, $R^2$ and X have the significance given above.

First route

The amide (I) can be prepared by reacting an amine (II) with an acylating reagent (III) with or without base (e.g. pyridine, triethylamine, sodium hydroxide) in the presence or absence of an inert solvent (e.g. water, methanol, benzene, dimethylformamide, dimethylsulfoxide) at room temperature or with heating.

Second route

Halogenation of the isoxazole (Ia) can be carried out in a conventional manner. The isoxazole (Ia) is treated with a halogenting agent (e.g. chlorine, bromine, sulfuryl chloride) in an inert solvent (e.g. acetic acid, methylene chloride, chloroform) at room temperature or with heating.

The present invention includes a process for the preparation of a compound in accordance with any one of the above routes.

Practical examples of the preparation of the isoxazole derivatives (I) in accordance with each of the above routes are illustrated in the following Synthetic Examples.

SYNTHETIC EXAMPLE 1

Propionic anhydride (5 ml) is added to 3-amino-5-t-butylisoxazole (2.52 g), and the resultant mixture is stirred at room temperature for 3 hours and then allowed to stand at room temperature overnight. The reaction mixture is poured onto icy water (50 ml). The precipitated crystals are filtered and shaken with benzene. The benzene layer is washed with saturated aqueous sodium hydrogen carbonate and water, each twice, dried over anhydrous sodium sulfate and evaporated to remove the solvent. The residue is recrystallized from cyclohexane to give N-(5-t-butyl-3-isoxazolyl)propionamide (2.91 g) as colorless crystals melting at 95.0° to 96.0° C.

SYNTHETIC EXAMPLES 2 TO 6

The following products (Ia) are obtained from the corresponding amines (II) by the reaction with the corresponding anhydride, $(R^2CO)_2O$, by procedures similar to that described in Example 1.

TABLE 1

| Syn. Ex. | R | $R^1$ | $R^2$ | m.p. or b.p. |
|---|---|---|---|---|
| 2 | t-Bu | H | —(CH$_2$)$_2$CH$_3$ | 67.0–68.5° C. |
| 3 | t-Bu | H | —(CH$_2$)$_3$CH$_3$ | 96.5–97.5° C. |
| 4 | t-Bu | H | —(CH$_2$)$_4$CH$_3$ | 72.0–73.5° C. |
| 5 | t-Bu | H | —CH(CH$_3$)$_2$ | 123.0–124.0° C. |

TABLE 1-continued

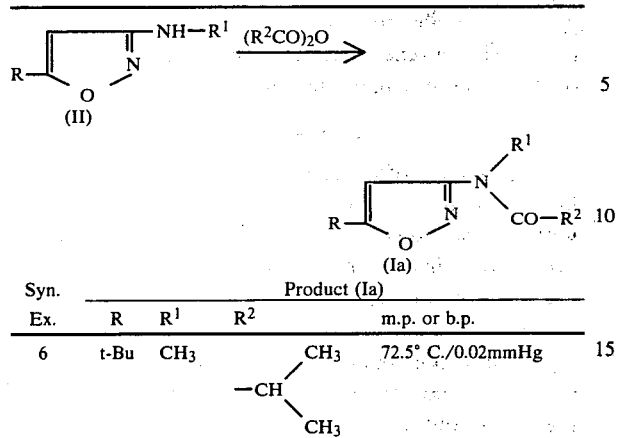

| Syn. Ex. | R | R¹ | R² | m.p. or b.p. |
|---|---|---|---|---|
| 6 | t-Bu | CH₃ | —CH(CH₃)(CH₃) | 72.5° C./0.02mmHg |

Note
The abbreviations in Table 1 have the following significance:
Bu (butyl),
t- (tertiary-),
m.p. (melting point),
b.p. (boiling point).

SYNTHETIC EXAMPLE 7

To a solution of 3-amino-5-t-butylisoxazole (2.80 g) in pyridine (10 ml) is dropwise added isobutyryl chloride (2.34 g) keeping the mixture below 10° C. The reaction mixture is stirred with cooling for 30 minutes and at room temperature for 1 hour and evaporated to remove the pyridine. The residue is mixed with 5% hydrochloric acid solution (40 ml) and shaken with methylene chloride. The methylene chloride layer is separated, washed with saturated aqueous sodium hydrogen carbonate and water, dried over anhydrous sodium sulfate and evaporated to remove the methylene chloride. The residue is chromatographed on a column of silica gel and recrystallized from n-hexane to give N-(5-t-butyl-3-isoxazolyl)isobutyramide (3.85 g) as colorless needles melting at 123.0° to 124.0° C.

SYNTHETIC EXAMPLES 8 TO 19

The reactions are each effected as in Example 7 to give the following products (Ia):

TABLE 2

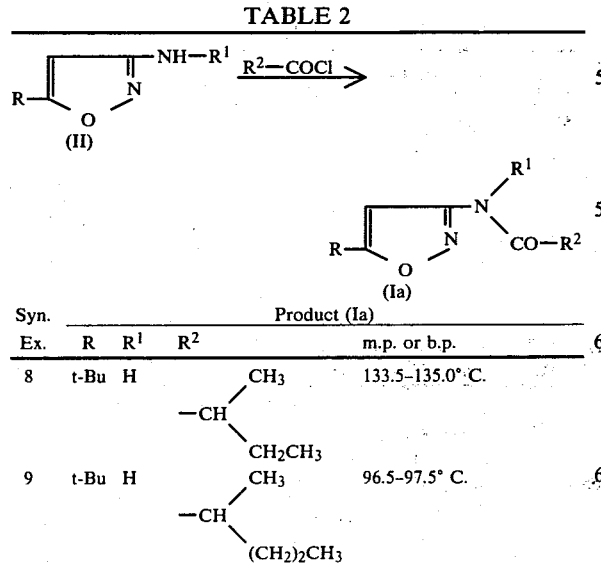

| Syn. Ex. | R | R¹ | R² | m.p. or b.p. |
|---|---|---|---|---|
| 8 | t-Bu | H | —CH(CH₃)(CH₂CH₃) | 133.5–135.0° C. |
| 9 | t-Bu | H | —CH(CH₃)((CH₂)₂CH₃) | 96.5–97.5° C. |

TABLE 2-continued

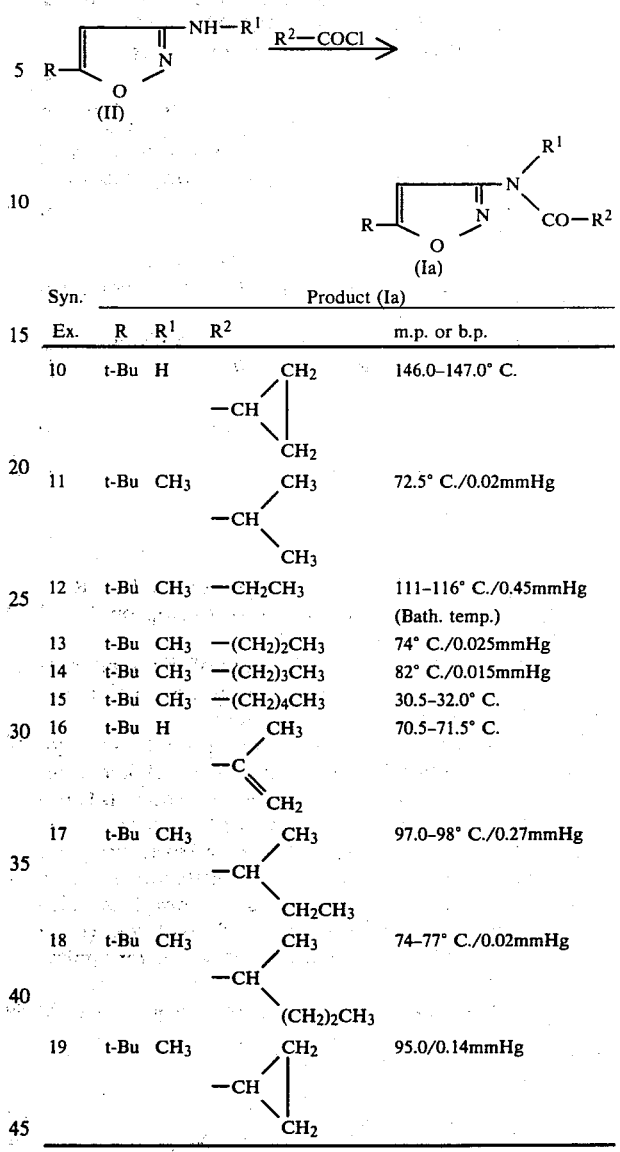

| Syn. Ex. | R | R¹ | R² | m.p. or b.p. |
|---|---|---|---|---|
| 10 | t-Bu | H | —CH(CH₂)(CH₂) | 146.0–147.0° C. |
| 11 | t-Bu | CH₃ | —CH(CH₃)(CH₃) | 72.5° C./0.02mmHg |
| 12 | t-Bu | CH₃ | —CH₂CH₃ | 111–116° C./0.45mmHg (Bath. temp.) |
| 13 | t-Bu | CH₃ | —(CH₂)₂CH₃ | 74° C./0.025mmHg |
| 14 | t-Bu | CH₃ | —(CH₂)₃CH₃ | 82° C./0.015mmHg |
| 15 | t-Bu | CH₃ | —(CH₂)₄CH₃ | 30.5–32.0° C. |
| 16 | t-Bu | H | —C(CH₃)(=CH₂) | 70.5–71.5° C. |
| 17 | t-Bu | CH₃ | —CH(CH₃)(CH₂CH₃) | 97.0–98° C./0.27mmHg |
| 18 | t-Bu | CH₃ | —CH(CH₃)((CH₂)₂CH₃) | 74–77° C./0.02mmHg |
| 19 | t-Bu | CH₃ | —CH(CH₂)(CH₂) | 95.0/0.14mmHg |

Note
The abbreviations in Table 2 are each as defined above for Table 1.

SYNTHETIC EXAMPLE 20

Methylene chloride (20 ml) and sulfuryl chloride (5.40 g) are added to N-(5-t-butyl-3-isoxazolyl)cyclopropanecarboxamide (4.17 g) and refluxed with heating for 1.5 hours. The methylene chloride and the unreacted sulfuryl chloride are evaporated under reduced pressure. The residue is chromatographed on a column of silica gel and recrystallized from benzene to give N-(5-t-butyl-4-chloro-3-isoxazolyl)cyclopropanecarboxamide (4.10 g) as colorless needles melting at 129.5° to 131.0° C.

SYNTHETIC EXAMPLES 21 TO 27

The reactions are each effected as in Example 20 to give the following products (Ib):

TABLE 3

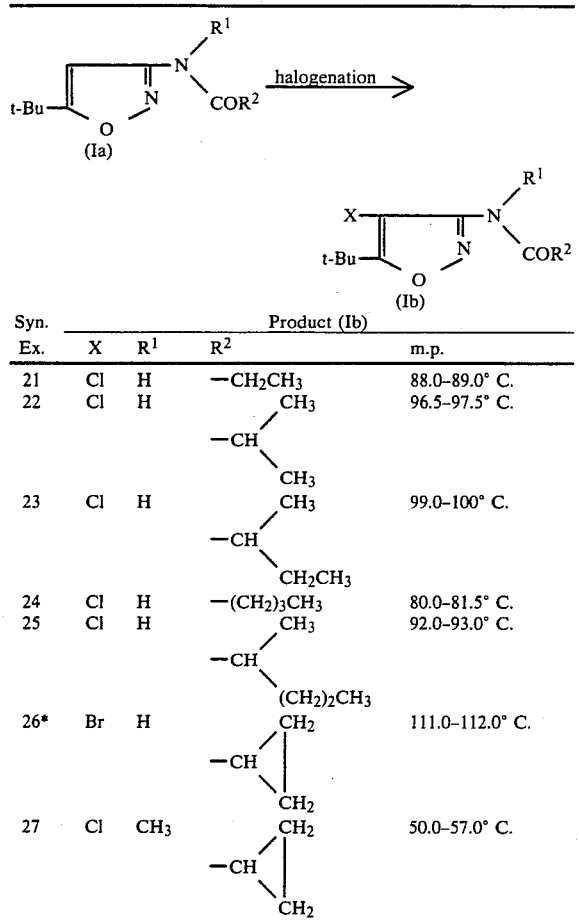

| Syn. Ex. | X | R¹ | Product (Ib) R² | m.p. |
|---|---|---|---|---|
| 21 | Cl | H | —CH₂CH₃ | 88.0–89.0° C. |
| 22 | Cl | H | —CH(CH₃)₂ | 96.5–97.5° C. |
| 23 | Cl | H | —CH(CH₃)(CH₂CH₃) | 99.0–100° C. |
| 24 | Cl | H | —(CH₂)₃CH₃ | 80.0–81.5° C. |
| 25 | Cl | H | —CH(CH₃)((CH₂)₂CH₃) | 92.0–93.0° C. |
| 26* | Br | H | —CH(CH₂)(CH₂) [cyclopropyl] | 111.0–112.0° C. |
| 27 | Cl | CH₃ | —CH(CH₂)(CH₂) [cyclopropyl] | 50.0–57.0° C. |

Note
*Bromine and 1,2-dichloroethane are used.

EXPERIMENT 1

(a) Compounds tested

| Compound No. | Compound |
|---|---|
| 1 | N-(5-t-butyl-3-isoxazolyl)propionamide |
| 2 | N-(5-t-butyl-3-isoxazolyl)isobutyramide |
| 3 | N-(5-t-butyl-3-isoxazolyl)-sec-valeramide |
| 4 | N-(5-t-butyl-3-isoxazolyl)valeramide |
| 5 | N-(5-t-butyl-3-isoxazolyl)-2-methylvaleramide |
| 6 | N-(5-t-butyl-3-isoxazolyl)hexanamide |
| 7 | N-(5-t-butyl-3-isoxazolyl)-2-methylhexanamide |
| 8 | N-(5-t-butyl-3-isoxazolyl)cyclopropanecarboxamide |
| 9 | N-methyl-N-(5-t-butyl-3-isoxazolyl)cyclopropanecarboxamide |
| 10 | PCP-Na (Sodium pentachlorophenoxide) |

(b) Test method (1) Pre-emergence test 25 seeds of a test plant were sown in sandy soil in a polyethylene cup (diameter: 9 cm). After sowing, the seeds were covered with sandy soil to about 5 mm depth and an aqueous suspension of a test compound at a concentration of 100 ppm using Tween 20 (trademark of Atlas Powder Co.) as a spreader was applied over the surface of the sandy soil. Application rate of the test compound was 10 g/are and 30 g/are, and the compound was applied in aqueous suspension (water dilution: 10 L/are) by a sprayer. Administration was effected at 25° C. in a greenhouse in the natural sunlight. Degree of germination was evaluated 3 weeks after the application.

(2) Post-emergence test

A test compound was applied to young plants 10 days after seeding. Administration and evaluation were effected as described above in (1).

(c) Method of the evaluation

Number of plants which survived was determined with the naked eye and the survival percentage for the sown seeds was obtained. The survival percentage was marked in six degrees as follows:

| Survival ratio of the plant tested | Mark(s) |
|---|---|
| Not more than 10% | 5 |
| 11–25% | 4 |
| 26–50% | 3 |
| 51–75% | 2 |
| 76–90% | 1 |
| Not less than 91% | 0 |

(d) Result

TABLE 4.

| Compound No. | Application rate (g/are) | Herbicidal Activity Pre-emergence test | | | | | | Post-emergence test | | | | | |
|---|---|---|---|---|---|---|---|---|---|---|---|---|---|
| | | A | B | C | D | E | F | A | B | C | D | E | F |
| 1 | 10 | 0 | 0 | 0 | 4 | 4 | 1 | 0 | 0 | 0 | 5 | 4 | 5 |
| | 30 | 0 | 2 | 3 | 5 | 5 | 5 | 0 | 1 | 2 | 5 | 5 | 5 |
| 2 | 10 | 0 | 3 | 5 | 5 | 5 | 5 | 0 | 1 | 5 | 5 | 5 | 5 |
| | 30 | 0 | 4 | 5 | 5 | 5 | 5 | 0 | 5 | 5 | 5 | 5 | 5 |
| 3 | 10 | 0 | 0 | 1 | 0 | 0 | 0 | 0 | 0 | 0 | 4 | 0 | 0 |
| | 30 | 0 | 3 | 4 | 4 | 4 | 1 | 0 | 0 | 5 | 5 | 5 | 3 |
| 4 | 10 | 0 | 0 | 2 | 2 | 2 | 2 | 0 | 1 | 4 | 3 | 4 | 5 |
| | 30 | 0 | 4 | 5 | 5 | 5 | 5 | 0 | 2 | 5 | 5 | 5 | 5 |
| 5 | 10 | 0 | 3 | 5 | 5 | 5 | 5 | 0 | 0 | 5 | 2 | 5 | 5 |
| | 30 | 0 | 5 | 5 | 5 | 5 | 5 | 0 | 3 | 5 | 5 | 5 | 5 |
| 6 | 10 | 0 | 0 | 2 | 3 | 1 | 1 | 0 | 1 | 5 | 5 | 3 | 3 |
| | 30 | 0 | 0 | 2 | 5 | 2 | 0 | 0 | 1 | 5 | 5 | 5 | 3 |
| 7 | 10 | 0 | 0 | 5 | 5 | 5 | 5 | 0 | 0 | 2 | 5 | 5 | 5 |
| | 30 | 0 | 4 | 5 | 5 | 5 | 5 | 0 | 0 | 2 | 5 | 5 | 5 |
| 8 | 10 | 0 | 5 | 5 | 5 | 5 | 5 | 0 | 5 | 5 | 5 | 5 | 5 |

TABLE 4.-continued

| Compound No. | Application rate (g/are) | Herbicidal Activity | | | | | | | | | | | |
|---|---|---|---|---|---|---|---|---|---|---|---|---|---|
| | | Pre-emergence test | | | | | | Post-emergence test | | | | | |
| | | A | B | C | D | E | F | A | B | C | D | E | F |
| | 30 | 0 | 5 | 5 | 5 | 5 | 5 | 3 | 5 | 5 | 5 | 5 | 5 |
| 9 | 10 | 1 | 2 | 2 | 5 | 5 | 5 | 3 | 2 | 4 | 5 | 5 | 5 |
| | 30 | 4 | 5 | 5 | 5 | 5 | 5 | 5 | 5 | 5 | 5 | 5 | 5 |
| 10 | 10 | 0 | 0 | 0 | 0 | 2 | 3 | 0 | 0 | 0 | 0 | 2 | 5 |
| | 30 | 0 | 0 | 0 | 0 | 2 | 3 | 0 | 0 | 0 | 0 | 4 | 5 |
| | 50 | 0 | 2 | 2 | 0 | 5 | 5 | 0 | 0 | 4 | 2 | 5 | 5 |

Note
The abbreviations have the following significance:
A (*Triticum aestivum*),
B (*Echinochloa crusgalli*),
C (*Digitaria adscendens*),
D (*Brassica campestris*),
E (*Polygonum logisetum*),
F (*Amaranthus retroflexus*).

Accordingly, the amides (I) (Compound Nos. 1 to 9) each showed hardly any herbicidal activity against *Triticum aestivum* but showed excellent and selective herbicidal activity against *Echinochloa crusgalli*, *Digitaria adscendens*, *Brassica campestris*, *Polygonum longisetum* and *Amaranthus retroflexus*, and their herbicidal activities are far more potent than that of a commercially available herbicide, PCP-Na (Compound No. 10)

EXPERIMENT 2

The toxicity of N-(5-t-butyl-3-isoxazolyl)isobutylramide was examined on *Oryzias latipes* and found to be very low in comparison with that of a commercially available PCP-Na.

EXPERIMENT 3

Herbicidal activity against *Echinochloa crusgalli* and *Monochoria vaginalis* under submerged paddy field conditions.

(a) Compound tested

| | Compound No. |
|---|---|
| 1. | N-(5-t-butyl-3-isoxazolyl)-2-methylpentanamide |
| 2 | N-(5-t-butyl-3-isoxazolyl)cyclopropanecarboxamide |
| 3 | N-methyl-N-(5-t-butyl-3-isoxazolyl)cyclopropanecarboxamide |
| 4 | Propanil (Control) |

(b) Test method

Into $2 \times 10^{-4}$ are of a Wagner pot, paddy field soil was placed, and water was poured therein to 3 cm deep. 25 seeds of a test plant were sown. Test compound was applied to *Echinochloa crusgalli* at the time of pre-emergence, first leaf stage, second leaf stage and third leaf stage and to *Monochoria vaginalis* at the time of pre-emergence, coleoptile stage, first leaf stage and second leaf stage. Application rate of a test compound included 6.25 g, 12.5 g, 25 g, 50 g, 75 g and 100 g each per are. The number of plants which survived was examined in comparison with that of the untreated section. The evaluation was marked in six degrees of survival ratio as in Experiment 1.

(c) Result

TABLE 5.

| Compound No. | Application rate (g/are) | Echinochloa crusgalli | | | | Monochoria vaginalis | | | |
|---|---|---|---|---|---|---|---|---|---|
| | | PRE | 1L | 2L | 3L | PRE | CO | 1L | 2L |
| 1 | 6.25 | 2 | 1 | 1 | 0 | 0 | 4 | 3 | 3 |
| | 12.5 | 2 | 3 | 3 | 0 | 0 | 5 | 4 | 3 |
| | 25 | 2 | 5 | 5 | 0 | 0 | 5 | 5 | 4 |
| | 50 | 3 | 5 | 5 | 2 | 2 | 5 | 5 | 5 |
| | 75 | 5 | 5 | 5 | 2 | 3 | 5 | 5 | 5 |
| | 100 | 5 | 5 | 5 | 4 | 3 | 5 | 5 | 5 |
| 2 | 6.25 | 3 | 5 | 5 | 5 | 4 | 5 | 5 | 5 |
| | 12.5 | 5 | 5 | 5 | 5 | 5 | 5 | 5 | 5 |
| | 25 | 5 | 5 | 5 | 5 | 5 | 5 | 5 | 5 |
| | 50 | 5 | 5 | 5 | 5 | 5 | 5 | 5 | 5 |
| | 75 | 5 | 5 | 5 | 5 | 5 | 5 | 5 | 5 |
| | 100 | 5 | 5 | 5 | 5 | 5 | 5 | 5 | 5 |
| 3 | 6.25 | 2 | 2 | 3 | 0 | 3 | 2 | 2 | 0 |
| | 12.5 | 4 | 5 | 5 | 2 | 5 | 5 | 5 | 1 |
| | 25 | 5 | 5 | 5 | 4 | 5 | 5 | 5 | 2 |
| | 50 | 5 | 5 | 5 | 5 | 5 | 5 | 5 | 5 |
| | 75 | 5 | 5 | 5 | 5 | 5 | 5 | 5 | 5 |
| | 100 | 5 | 5 | 5 | 5 | 5 | 5 | 5 | 5 |
| 4 | 6.25 | 0 | 0 | 0 | 0 | 0 | 2 | 1 | 1 |
| | 12.5 | 1 | 1 | 0 | 0 | 0 | 2 | 2 | 1 |
| | 25 | 3 | 2 | 1 | 0 | 0 | 2 | 2 | 2 |
| | 50 | 4 | 2 | 1 | 0 | 0 | 3 | 3 | 3 |
| | 75 | 4 | 3 | 2 | 0 | 2 | 4 | 3 | 3 |
| | 100 | 5 | 3 | 2 | 0 | 2 | 4 | 3 | 3 |

Note
The abbreviations have the following significance:
PRE (pre-emergence),
1L (first leaf stage),
2L (second leaf stage),
3L (third leaf stage),
CO (coleoptile stage).

(d) Conclusion

Accordingly, the subject matter of this invention (Compound Nos. 1-3) showed excellent herbicidal activity against *Echinochloa crusgalli* and *Monochoria vaginalis* under submerged paddy field conditions in comparison with a commercially available herbicide, propanil.

Additionally, chemical poisoning of rice plants by all test compounds (Compound Nos. 1-4) was almost not or never observed.

The present isoxazole derivatives (I) show excellent herbicidal activity against various grasses for a small rate of application. These compounds can also be used as non-selective or selective herbicides by changing the rate of application thereof. The herbicides of this invention are generally applicable to various crops including wheat, barely, corn, carrots, peanuts, peas or rice plants in order to protect them from unfavorable weeds and grasses. They can also be applied to sugar cane, potatoes, sweet potatoes, mentha, eggplant, or Spanish paprica after planting thereof. Virtually no chemical harm at all is observed as a result of the action of the present herbicides on these crops, such effects as are observed being so slight as to be easily recoverable. Furthermore, the present herbicides are quite harmless to humans and domestic animals, and they also show very low toxicity towards fishes, including shellfish. Thus, the herbicides of the present invention have a very high degree of safety and also exhibit a suitable amount of residual compound remaining in the soil after their use.

The invention includes a herbicidal composition which comprises a compound in accordance with the invention and a diluent, carrier or excipient.

The present herbicidal compositions may, for example, be prepared by mixing the effective isoxazole derivative (I) with an inert solid or liquid carrier, optionally in combination with a further adjuvant (e.g. emulsifiers, stabilizers, dispersants, suspending agents, spreaders, penetrants or wetting agents) and converting the resultant mixture into the desired preparation form (e.g. emulsion, wettable powders, granules, dusts or tablets). Examples of suitable carriers are solid carriers (e.g. clay, talc, diatomaceous earth or bentonite) and liquid carriers (e.g. water, alcohols, acetone, benzene, toluene, xylene, solvent naphtha or cyclohexane).

The herbicidal compositions of this invention may also include, and the present compounds can be used with, agricultural chemicals (e.g. insecticides, fungicides or other herbicide), manuring ingredients (e.g. ammonia sulfate or urea) or soil treating agents.

The invention also includes a method of killing a plant which method comprises applying thereto an effective amount of a compound in accordance with the invention or of a composition in accordance with the invention.

Presently preferred and practical embodiments of the present invention are illustrated in the following examples.

EXAMPLE A

N-methyl-N-(5-t-butyl-3-isoxazolyl)cyclopropanecarboxamide (10 parts by weight), Sorpol (Registered trademark; made by Toho Chemical Industry, Co., Ltd.) (10 parts by weight), cyclohexane (20 parts by weight) and solvent naphtha (60 parts by weight) are mixed, whereby an emulsion is obtained.

EXAMPLE B

N-(5-t-butyl-3-isoxazolyl)isobutyramide (50 parts by weight), calcium ligninsulfonate (3 parts by weight), Sorpol (Registered trademark; made by Toho Chemical Industry, Co., Ltd.) (3 parts by weight) and diatomaceous earth (44 parts by weight) are mixed and pulverized, whereby wettable powder is obtained.

EXAMPLE C

N-(5-t-butyl-3-isoxazolyl)-2-methylvaleramide (5 parts by weight) and clay (95 parts by weight) are mixed and pulverized, whereby a dust is obtained.

EXAMPLE D

N-(5-t-butyl-3-isoxazolyl)cyclopropanecarboxamide (5 parts by weight), calcium ligninsulfonate (5 parts by weight), bentonite (30 parts by weight) and clay (60 parts by weight) are mixed, pulverized, mixed with water, kneaded, granulated and dried, whereby granules are obtained.

What is claimed is:

1. A herbicidal composition comprising a compound represented by the formula:

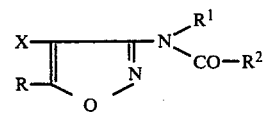

wherein R is t-butyl; $R^1$ is hydrogen or methyl; $R^2$ is alkyl ($C_2$ to $C_6$), alkenyl ($C_3$ to $C_4$) or cyclopropyl; and X is hydrogen or halogen, and an inert carrier.

2. The composition according to claim 1, containing N-(5-t-butyl-3-isoxazolyl)propionamide.

3. The composition according to claim 1, containing N-(5-t-butyl-3-isoxazolyl)isobutyramide.

4. The composition according to claim 1, containing N-(5-t-butyl-3-isoxazolyl)-sec-valeramide.

5. The composition according to claim 1, containing N-(5-t-butyl-3-isoxazolyl)valeramide.

6. The composition according to claim 1, containing N-(5-t-butyl-3-isoxazolyl)-2-methylvaleramide.

7. The composition according to claim 1, containing N-(5-t-butyl-3-isoxazolyl)hexanamide.

8. The composition according to claim 1, containing N-(5-t-butyl-3-isoxazolyl)-2-methylhexanamide.

9. The composition according to claim 1, containing N-(5-t-butyl-3-isoxazolyl)cyclopropanecarboxamide.

10. The composition according to claim 1, containing N-methyl-N-(5-t-butyl-3-isoxazolyl)cyclopropanecarboxamide.

11. A method of killing a plant which comprises applying thereto a herbicidally effective amount of a compound represented by the formula:

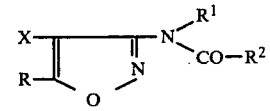

wherein R is t-butyl; $R^1$ is hydrogen or methyl; $R^2$ is alkyl ($C_2$ to $C_6$), alkenyl ($C_3$ to $C_4$) or cyclopropyl; and X is hydrogen or halogen.

* * * * *